United States Patent
Shukla

(10) Patent No.: US 12,383,419 B2
(45) Date of Patent: Aug. 12, 2025

(54) STOMAL DEVICE

(71) Applicant: Parul J. Shukla, New York, NY (US)

(72) Inventor: Parul J. Shukla, New York, NY (US)

(*) Notice: Subject to any disclaimer, the term of this patent is extended or adjusted under 35 U.S.C. 154(b) by 426 days.

(21) Appl. No.: 18/001,790

(22) PCT Filed: Jun. 16, 2021

(86) PCT No.: PCT/US2021/037672
§ 371 (c)(1),
(2) Date: Dec. 14, 2022

(87) PCT Pub. No.: WO2021/257732
PCT Pub. Date: Dec. 23, 2021

(65) Prior Publication Data
US 2023/0233356 A1     Jul. 27, 2023

Related U.S. Application Data

(60) Provisional application No. 63/039,507, filed on Jun. 16, 2020.

(51) Int. Cl.
*A61F 5/445* (2006.01)
*A61F 5/44* (2006.01)

(52) U.S. Cl.
CPC ...... *A61F 5/445* (2013.01); *A61F 2005/4455* (2013.01)

(58) Field of Classification Search
CPC ..... A61F 5/445; A61F 2005/4455; A61F 5/44
See application file for complete search history.

(56) References Cited

U.S. PATENT DOCUMENTS

| | | | | |
|---|---|---|---|---|
| 2,510,766 A | * | 6/1950 | Surface | A61F 5/445 600/32 |
| 4,217,664 A | * | 8/1980 | Faso | A61F 2/0063 600/32 |
| 4,671,272 A | * | 6/1987 | Steer | A61B 90/00 606/1 |
| 4,828,553 A | * | 5/1989 | Nielsen | A61F 5/448 604/339 |
| 6,716,209 B2 | * | 4/2004 | Leiboff | A61B 90/00 606/1 |
| 7,001,367 B2 | * | 2/2006 | Arkinstall | A61F 5/445 604/337 |
| 7,765,007 B2 | * | 7/2010 | Martino | A61N 1/36007 607/40 |

(Continued)

OTHER PUBLICATIONS

Pine James et al, "Intestinal Stomas", Surgery, Medicine Publishing, Abington, Elsevier Imprint, GB, vol. 35, No. 33, Feb. 8, 2017, p. 165-170, XP029926564, ISSN: 0263-9319, DOI: 10.1016/J.MPSUR.2016.12.002.

(Continued)

*Primary Examiner* — Guy K Townsend
(74) *Attorney, Agent, or Firm* — Kim IP Law Group LLC

(57) ABSTRACT

A stomal device for facilitating reversal of a stoma. The stomal device includes a hollow body, a pin, and a wafer. The body has an inner flap and an outer flap. The pin secures a bowel of a patient during retraction and withdrawal. The wafer is connectable to the body for forming a barrier between the bowel and an abdominal wall of a patient to prevent the formation of scar tissue and infection.

25 Claims, 18 Drawing Sheets

(56) References Cited

U.S. PATENT DOCUMENTS

| | | | | |
|---|---|---|---|---|
| 8,821,465 | B2* | 9/2014 | Hanuka | A61F 5/4407 604/333 |
| 8,864,729 | B2* | 10/2014 | Hanuka | A61F 5/443 604/334 |
| 8,998,862 | B2* | 4/2015 | Hanuka | A61F 5/4405 604/318 |
| 10,537,461 | B2* | 1/2020 | Hanuka | A61F 5/441 |
| 11,166,838 | B2* | 11/2021 | Cline | A61F 5/445 |
| 11,510,677 | B1* | 11/2022 | Leiboff | A61B 90/08 |
| 2003/0163121 | A1* | 8/2003 | Leiboff | A61B 90/00 606/1 |
| 2013/0324800 | A1* | 12/2013 | Cahill | A61B 17/3423 600/204 |
| 2019/0133813 | A1* | 5/2019 | Cline | A61F 5/445 |
| 2020/0038229 | A1* | 2/2020 | Aravalli | A61B 17/02 |
| 2021/0121317 | A1* | 4/2021 | Brönnimann | A61F 5/449 |
| 2022/0054297 | A1* | 2/2022 | Cline | A61F 5/445 |
| 2023/0233356 | A1* | 7/2023 | Shukla | A61F 5/445 604/332 |

OTHER PUBLICATIONS

Written Opinion of International Search Reporting in International Application No. PCT/US2021/037672 mailed Oct. 6, 2021.
International Search Report in International Application No. PCT/US2021/037672 mailed Oct. 6, 2021.

\* cited by examiner

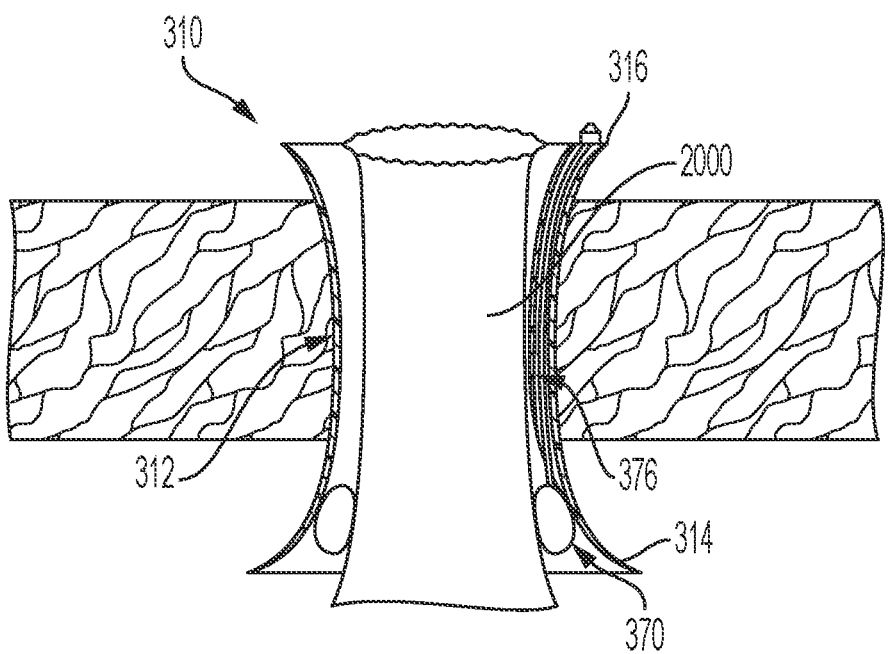
FIG. 18
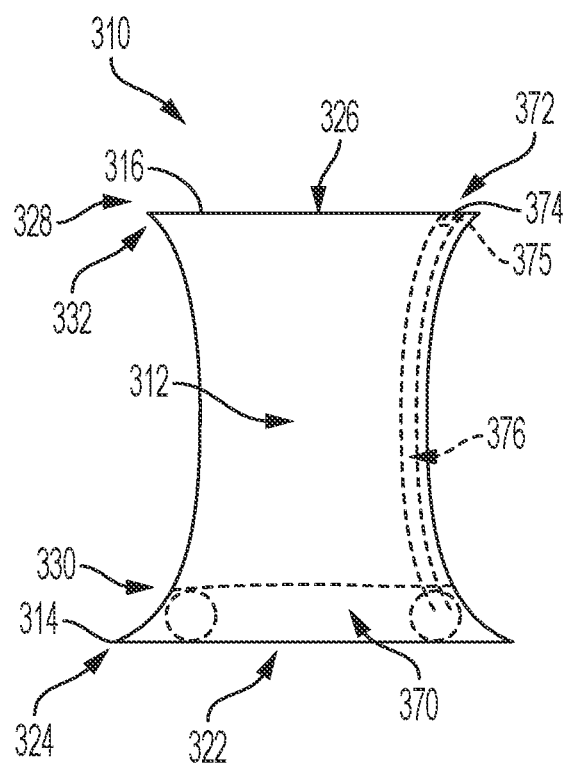 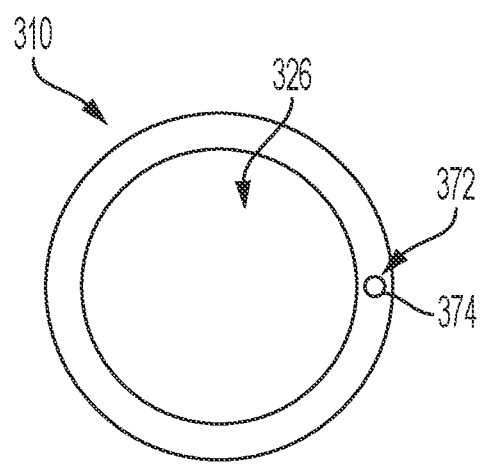
FIG. 19A  FIG. 19B

STOMAL DEVICE

FIELD OF THE INVENTION

Exemplary embodiments of the subject disclosure relate generally to a stomal device for assisting in the reversal/closure of a loop stoma as well as enabling intermittent continence to an end stoma, and in particular but not limited to the closure of stomas created during commonly performed surgical procedures such as an ileostomy or colostomy.

BACKGROUND OF THE DISCLOSURE

A colostomy refers to a surgical procedure to create an opening in the large intestine (i.e., the colon) through the abdomen. Likewise, an ileostomy refers to a surgical procedure to create an opening into the small intestine (i.e., the ileum) through the abdomen. A colostomy or ileostomy can be temporary or permanent. Traditional temporary ileostomy and colostomy procedures typically involve the creation of a stoma (e.g., a temporary stoma) connecting the bowel to the surface of the abdomen to allow fecal matter to be evacuated into a pouch, e.g., a stoma bag. A stoma may be a loop stoma or an end stoma, depending on the portion of the bowel that needs to be accessed. In the case of a temporary stoma, the reversal/closure of a stoma is often accompanied by a subsequent surgical procedure.

BRIEF SUMMARY OF THE DISCLOSURE

The subject disclosure describes a stomal device i.e., a stomal medical device and a method for reversing a loop stoma using the stomal device associated with a loop ileostomy or colostomy, or reversing an end stoma associated with an end ileostomy or colostomy, e.g., via in a minimally invasive surgical technique.

The subject disclosure provides a stomal device e.g., for facilitating reversal of a stoma. The stomal device can include a modularly constructed hollow body, a pin, and/or a wafer. The modularly constructed hollow body includes an inner flap or first flange and an outer flap or second flange. The pin is operable to secure a bowel of a patient during retraction and withdrawal about the stoma. The wafer is connectable to the hollow body and/or second flange for forming a barrier between the bowel and an abdominal wall of a patient to prevent the formation of scar tissue and infection.

In accordance with an aspect of the exemplary embodiment, the stomal device optionally includes a pouch. The pouch is attachable to the second flange and/or wafer, and can be removably attached to the second flange and/or wafer. Another aspect of the exemplary embodiment is that the hollow body of the stomal device is of unitary or modular construction. The hollow body is a pliable, flexible, and/or resilient material to facilitate its assembly and disassembly, but can alternatively be formed from a suitable rigid material.

In accordance with an exemplary embodiment, the stomal device is used to reverse a loop stoma associated with a loop ileostomy or colostomy. Steps of the installation procedure for the stomal device include: placing the stomal device at a pre-determined site, either intact or in a modular fashion; pulling a loop of a bowel of a patient through an abdominal wall; and inserting a pin below the loop of the bowel and into a flange or a portion of the hollow body of the stomal device for securing the bowel loop in position. The installation can also include the step of securing a wafer of the stomal device to the skin of a patient. When the stoma is to be reversed, the pin is removed, and the stomal device is disassembled, e.g., in a modular fashion and/or removed from through the surgical incision site. The present stomal device is designed to ensure ease of use and allows for a rapid surgical procedure to reverse a loop stoma in the operating room, or even in an office or clinic setting. Advantageously, such a rapid surgical procedure can eliminate the need for post-operative hospitalization to recover from said procedure.

In accordance with another exemplary embodiment, the subject disclosure discloses a stomal device for facilitating reversal of a stoma that includes a hollow body, an inner flap or first flange having a balloon, and an outer flap or second flange. The balloon is operable to compress an end portion of a bowel passing through the inner flap or first flange so as to provide temporary continence for the bowel.

In accordance with another exemplary embodiment, the subject disclosure discloses a stomal device comprising an elongated hollow body having a first open end about its first end and a second open end in fluid communication with the first open end about its second end opposite the first end, a first flange extending from the first end of the hollow body, a second flange extending from the second end of the hollow body, and a pin for extending through the second flange transverse to a longitudinal direction of the hollow body.

According to an aspect, the hollow body is substantially tubular. According to another aspect, the hollow body is curved cone shaped. According to another aspect, the hollow body includes a pair of curved cone shaped portions. According to another aspect, the hollow body is flexible. According to an aspect, the hollow body is formed from silicone or other inert and non-reactive materials.

According to an aspect, the hollow body is modular. According to another aspect, the hollow body comprises a first body portion connectable to a second body portion.

According to an aspect, the first flange is a tapered flange. According to another aspect, the tapered flange includes a tubular inner side and tapered outer side. According to another aspect, the second flange includes a substantially circular rib extending from its outer side.

According to an aspect, the stomal device further comprises a wafer adjacent the second flange. According to another aspect, the wafer includes a central opening in fluid communication with the second open end.

According to an aspect, the stomal device further comprises a pouch that includes an opening attachable to the first flange such that the opening is in fluid communication with the first open end.

According to an aspect, the first flange has an overall diameter greater than the second flange. According to another aspect, the second flange includes opposed through holes for receiving a pin therein. According to another aspect, the pin has a length greater than an overall diameter of the second flange.

According to an aspect, the stomal device further comprises a balloon extending from the first flange. According to another aspect, the stomal device further comprises a nozzle operatively connected to the balloon having an inlet adjacent the second flange.

According to an aspect, the stomal device further comprises a balloon carried by an interior of the hollow body. According to another aspect, the stomal device further comprises a plurality of extendable arms adjacent the first flange.

According to an aspect, the hollow body comprises an inner body member and an outer body member, and wherein one of the inner body member and the outer body member is movable relative to the other. According to another aspect, the outer body member includes a lower end having an annular gear. According to another aspect, the stomal device further comprises a plurality of extendable arms each having a spur gear engaged with the annular gear. According to another aspect, the stomal device further comprises a locking mechanism for securing the outer body member in a fixed position relative to the inner body member.

Other features and advantages of the subject disclosure will be apparent from the following more detailed description of the exemplary embodiments.

BRIEF DESCRIPTION OF THE SEVERAL VIEWS OF THE DRAWINGS

The following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

FIG. 18 is an elevational cross-sectional view of another exemplary embodiment of a stomal device in accordance with the subject disclosure implanted in an incision;

FIG. 19A is an elevational view of the stomal device of FIG. 18;

FIG. 19B is a top plan view of the stomal device of FIG. 18;

DETAILED DESCRIPTION OF THE DISCLOSURE

Figure 1:
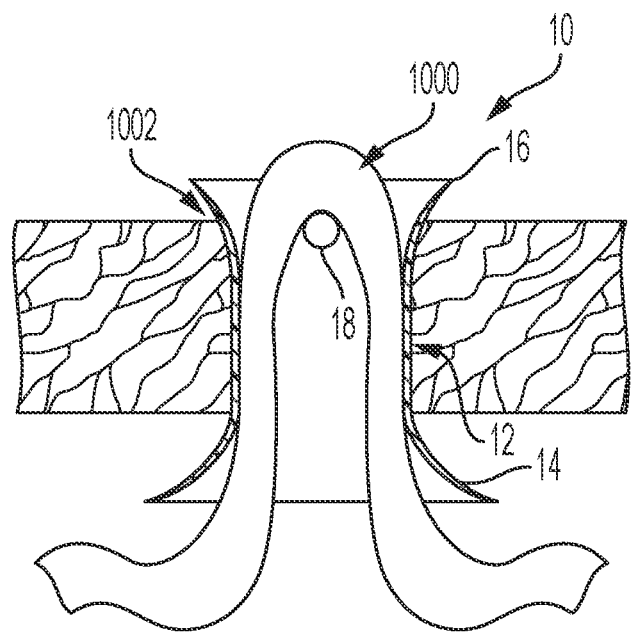
FIG. 1 is an elevational cross-sectional view of an exemplary embodiment of a stomal device in accordance with the subject disclosure implanted in an incision.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The term "anterior" means in front of the center of a body. The term "posterior" means behind the center of a body and/or away from the "anterior" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

Certain terminology is used in the following description for convenience only and is not limiting. The words "right," "left," "upper," and "lower" designate directions in the drawings to which reference is made. The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

The present stomal device allows for the closure of a stoma (temporary stoma) without the need for a strenuous surgical procedure that often requires post-operative hospitalization associated with several days for recovery. That is, the stomal device allows a medical provider to effectuate the reversal of a stoma in a more convenient and non-invasive setting such as an office or clinic. The stomal device allows for a stoma reversal in a sophisticated manner that achieves the goals of a surgical procedure in a minimally invasive manner and assists with rapid recovery from a surgical procedure.

Figure 2:
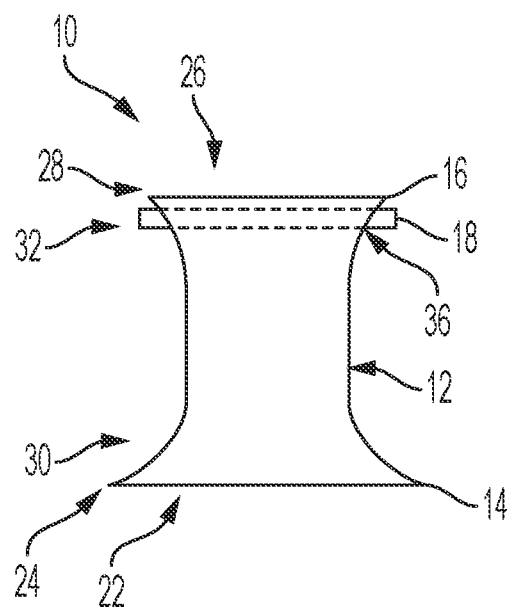
FIG. 2 is an elevational view of the stomal device of FIG. 1.
Figure 9:
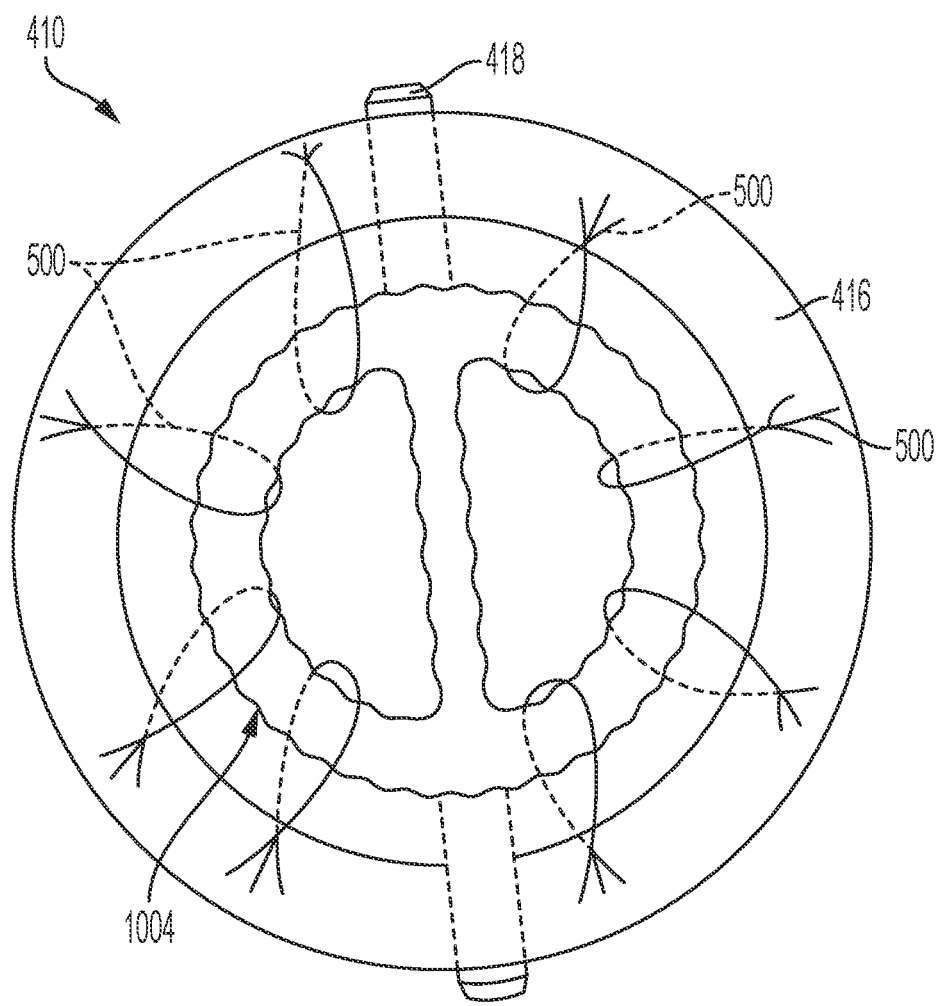
FIG. 9 is another top view of the stomal device of FIG. 4 implanted in an incision.

Referring now to the drawings, FIGS. 1, 2 and 9 illustrate an exemplary embodiment of a stomal device 10 in accordance with the subject disclosure. The stomal device 10 includes an elongated hollow body 12, a first flange or flap 14 extending from the hollow body, a second flange or flap 16 extending from the hollow body, and a pin 18 for extending through the second flange.

Figure 6:
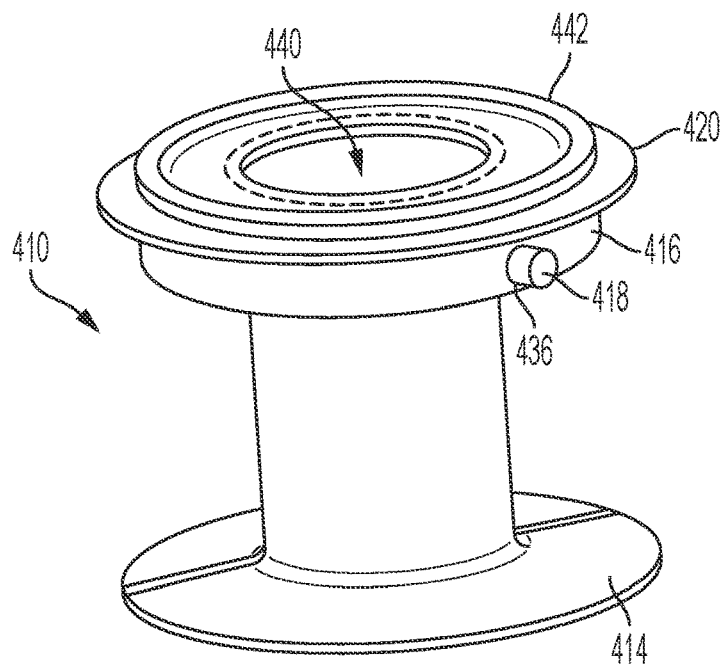
FIG. 6 is a perspective view of the stomal device of FIG. 4.

The elongated hollow body 12 is generally configured as best shown in FIGS. 1, 2, and 6. The hollow body includes a first open end 22 about its first end 24 and a second open end 26 about its second end 28 opposite the first end. The first and second open ends are in fluid communication. The hollow body 12 is substantially tubular. As shown in FIG. 2, the hollow body can be configured to have a curved cone shape including substantially curved cone shaped ends or portions 30, 32. The hollow body is structured to have an average overall height of about 5.0 to 6.0 cm, including 4.9, 5.1, 5.2, 5.3, 5.4, 5.5, 5.6, 5.7, 5.8, 5.9, 6.1 and 6.2 cm, thereby accommodating patients of varies sizes e.g., in a thin patient the height of the hollow body can be smaller and for an obese patient the height of the hollow body can be larger. The hollow body is also structured to have an inner diameter or aperture opening size from about 2.5 to 3.0 cm, including 2.4, 2.6, 2.7, 2.8, 2.9, and 3.1 cm or more e.g., to accommodate larger patients where a larger inner diameter may be required. Further, about its mid-section, the hollow body is structured to have an overall inner diameter of about 2.4-2.6 cm, which is smaller than the overall diameter of the hollow body about its respective ends.

The hollow body can be flexible and formed from a resilient, pliable material. For example, the hollow body can be formed from a medical grade polymer e.g., silicone, polytetrafluoroethylene (PTFE), perfluoroalkoxy alkanes (PFA), THV (a polymer of tetrafluoroethylene, hexafluoropropylene and vinylidene fluoride), polyamide (PA), ethylene vinyl acetate (EVA), cyclic olefin copolymers (COCS), flexible polyvinyl chloride (PVC), flexible polyurethane, or other inert and non-reactive materials. Alternatively, the hollow body can be formed of suitable rigid materials, such as metal, a rigid polymer, e.g., polyethylene (PE), polyether ether ketone (PEEK), polyvinylidene difluoride (PVDF), rigid polyvinyl chloride (PVC), rigid polyurethane, or a composite.

Figure 3A:
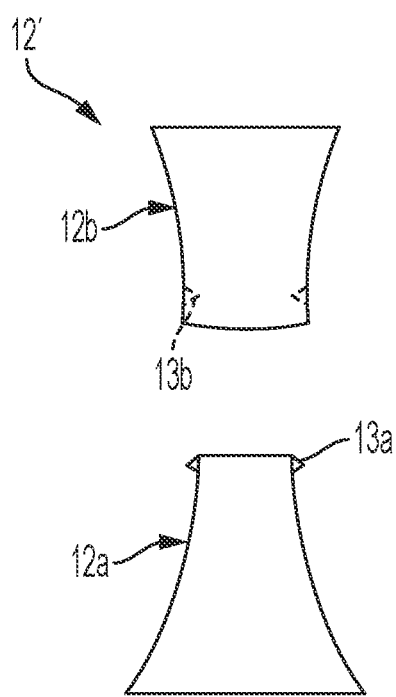
FIG. 3A is an elevational view of a modular stomal device in accordance with another exemplary embodiment of the subject disclosure in a disassembled state.
Figure 3B:
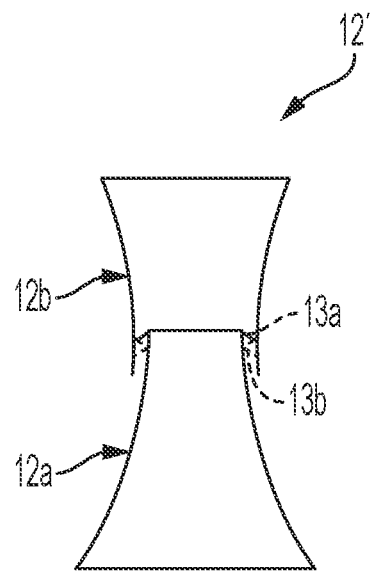
FIG. 3B is an elevational view of the stomal device of FIG. 3A in an assembled state.

In accordance with another exemplary embodiment of the stomal device, the hollow body can be configured as a modular hollow body 12', as shown in FIGS. 3A and 3B. In this exemplary embodiment, the modular hollow body 12' includes a first hollow body portion 12a and a second hollow body portion 12b that is connectable or attachable to the first hollow body portion. The modular hollow body is segmented about its mid-portion. That is, the first and second hollow body portions are connected together about the modular hollow body's mid-portion e.g., via a fastener, such as a detent or cooperating detents 13a, 13b on the first and second hollow body portions. Such a modular construction facilitates implantation and explantation of the stomal device while reducing the need for a large incision at the stoma site.

Referring back to FIGS. 1 and 2, the first flange 14 or inner flap is a radially extending flange that extends from a first end of the hollow body 12. The first flange 14 can be a tapered flange and have a tubular or curved cone shaped inner side and a tapered outer side such that it gradually extends outwardly from the first end forming a substantially curved cone shaped end, or it can alternatively be configured as a substantially planar flange extending radially outwardly.

The second flange 16 or outer flap is a radially extending flange that extends from a second end of the hollow body 12. The second flange 16 can be a tapered flange and have a tubular or curved cone shaped inner side and a tapered outer edge such that it gradually extends outwardly from the second end forming a substantially curved cone shaped end, or it can alternatively be configured as a substantially planar flange extending radially outwardly. According to an aspect, the first flange 14 of the hollow body 12 has an overall diameter greater than the second flange 16. For instance, the first flange can have an overall diameter of from about 6.5 to 7.5 cm, including 6.4, 6.6, 6.7, 6.8, 6.9, 7.0, 7.1, 7.2, 7.3, 7.4, and 7.6 cm, whereas the second flange can have an overall diameter of from about 5.0 to 6.0 cm, including 4.9, 5.1, 5.2, 5.3, 5.4, 5.5, 5.6, 5.7, 5.9 and 6.1 cm. The first flange is preferably larger in diameter than the second flange such that, when the hollow body is inserted into the incision, the stomal device is self-retaining in the incision and resists dislodgement from the body cavity.

The opposed through holes 36 (FIG. 2) can be formed in the hollow body of the stomal device. The opposed through holes 36 extend through the side wall of the hollow body such that its longitudinal axis traverses a longitudinal direction of the hollow body. The opposed through holes are preferably positioned about a medial region of the hollow body. The opposed through holes can alternatively be configured to pass through the second flange. As such, when the pin 18 is received within the opposed through holes, a longitudinal axis of the pin traverses the longitudinal direction of the hollow body. Preferably, the stomal device is configured such that a central longitudinal axis of the pin is substantially perpendicular to a central longitudinal axis of the hollow body.

Referring to FIGS. 1 and 2 the pin is structured to pass through the opposed through holes 36 (FIG. 2) in or adjacent the second flange 16 for releasably retaining a portion of an internal organ, e.g., an extracted loop of the bowel 1000 (FIG. 1), exteriorly of the surgical incision. That is, the pin 18 is inserted beneath the bowel loop 1000 to prevent the bowel loop from sinking back into the abdomen of a patient. The pin 18 controls retraction and withdrawal of the bowel during treatment of a patient. When access to the bowel is no longer needed, the pin 18 can be removed to allow the bowel loop to sink back into the abdomen.

Figure 8:
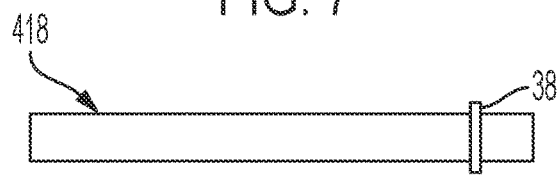
FIG. 8 is a side view of a pin applicable to the stomal device of the subject disclosure.

The pin 18 is configured as a rod having a substantially cylindrical rod shape with an overall length of about 6 to 8 cm and an overall diameter of about 4 to 6 mm. The pin preferably has a length greater than an overall diameter of the second flange 16 to facilitate removal of the pin from the second flange. The pin's overall diameter is preferably constant throughout its entire length. The pin 18 can also include a stop 38 (FIG. 8), such as a radial rib for preventing the pin from falling out of or pass the opposing through holes. In accordance with an aspect, the pin is formed from a rigid material suitable for sterilization, such as a metal or rigid polymer.

Figure 4:
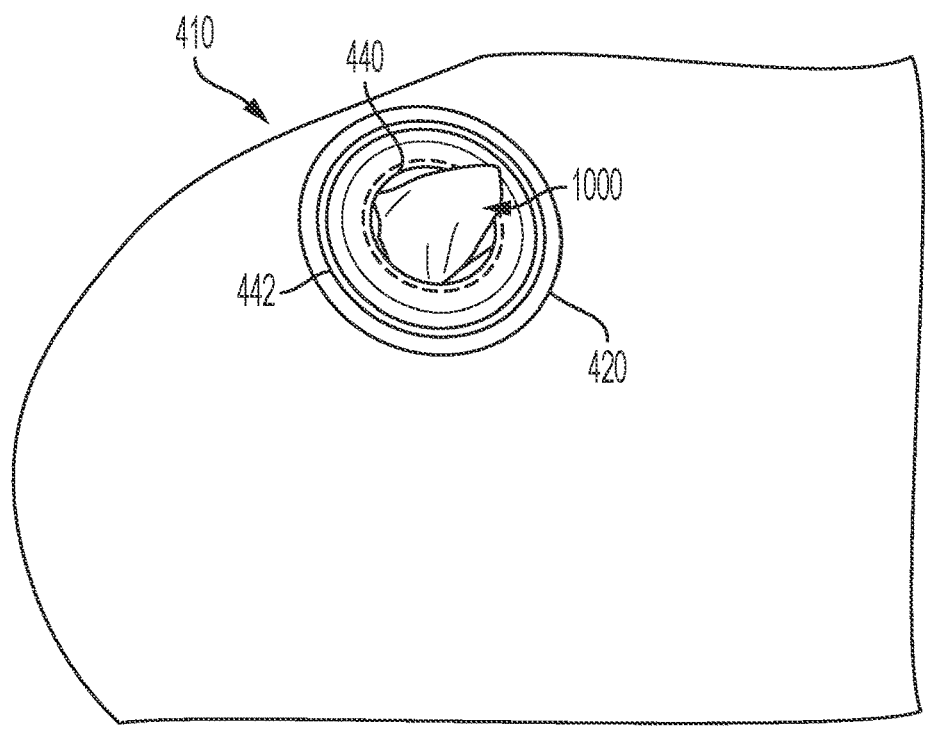
FIG. 4 is a top view of another exemplary embodiment of a stomal device in accordance with the subject disclosure implanted in an incision.
Figure 7:
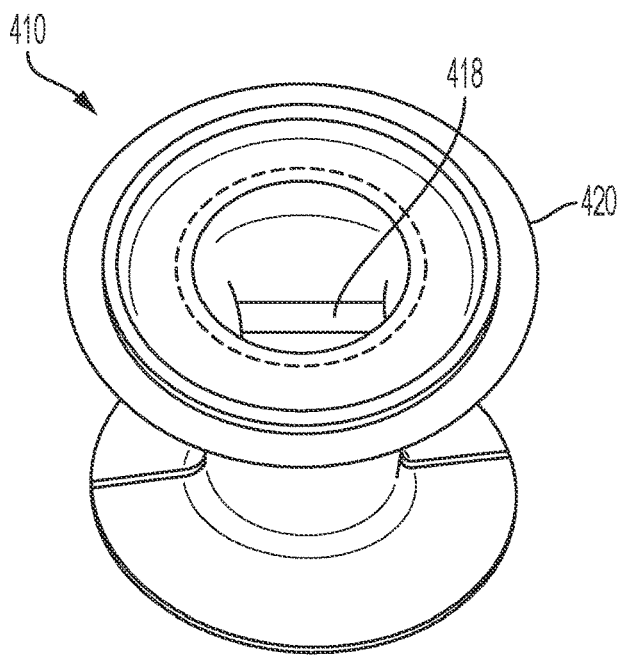
FIG. 7 is a top perspective view of the stomal device of FIG. 4.

FIGS. 4, 6 and 7 illustrate another exemplary embodiment of a stomal device 410 in accordance with the subject disclosure. The stomal device 410 is similar to stomal device 10 and includes an elongated hollow body 412, a first flange 414, a second flange 416, and a pin 418. The stomal device 410 additionally comprises a wafer 420 positionable adjacent the second flange 416. The wafer 420 may be of an annular flange or other radially projecting rim, collar, disc or rib configuration. A central opening 440 of the wafer is in fluid communication with and sized to substantially match a second open end of the hollow body 412. Additionally, the overall diameter of the wafer is sized to substantially match that of the second flange. The wafer 420 also includes an upwardly extending annular rib 442 spaced from its outer circumferential edge to facilitate connection to an optional pouch 444, further described below. The annular rib sits proud of an upper surface of the wafer. The wafer 420 can be formed from substantially rigid reinforced or unreinforced medical grade polymer, cardboard, metal, or other suitable materials.

The wafer 420 is a barrier applied to the skin adjacent the hollow body 412. The wafer 420 is configured to separate a portion of a body organ, e.g., the bowel, from a surgical incision 1002 (FIG. 1). The wafer advantageously separates the incision (and skin) from the bowel so as to prevent or retard formation of scar tissue around the stoma. Otherwise, if scar tissue is permitted to form, surgery may be required to detach the bowel from the abdominal wall (or skin). The wafer 420 may be applied to the skin using a bio-compatible adhesive or other suitable fastener.

The stomal device of the subject disclosure including the first and second flanges can be configured to have an overall height of about 5.0 to 6.0 cm, including 4.9, 5.1, 5.2, 5.3, 5.4, 5.5, 5.6, 5.7, 5.9, and 6.1 cm, although in a thin patient the height of the hollow body can be smaller and for an obese patient the height of the hollow body can be larger, and an overall height or thickness of the wafer of about 1.0 to 4.0 mm, including 0.9, 1.2, 1.4, 1.6, 1.8, 2.0, 2.2, 2.4, 2.6, 2.8, 3.2, 3.4, 3.6, 3.8 and 4.1 mm. The overall diameter of the stomal device can range from 5.0 to 7.5 cm, including 4.8, 5.2, 5.4, 5.6, 5.8, 6.0, 6.2, 6.4, 6.6, 6.8, 7.0, 7.2, 7.4 and 7.6 cm, and preferably tapers inwardly about its mid-section to an outer diameter of about 2.9 to 3.3 cm, including 2.7, 2.8, 3.0, 3.1, 3.2 and 3.4 cm.

Figure 5:
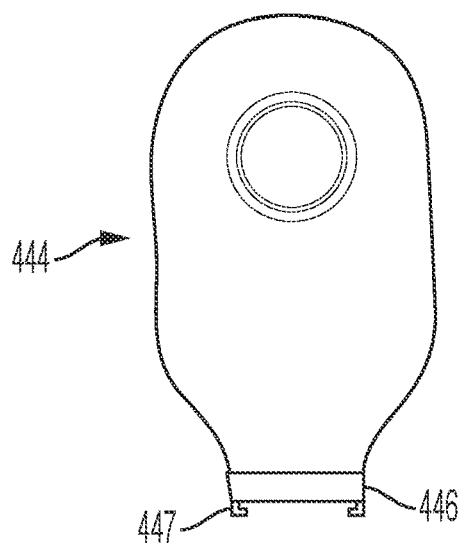
FIG. 5 is an elevational view of a pouch adapted for use with the stomal device of FIG. 4.

Referring to FIG. 5, the stomal device 410 can optionally include a pouch 444 to enable removal and disposal of fluid and/or waste material from the patient. The pouch includes an opening 446 attachable to the annular rib of the wafer such that the opening is in fluid communication with the second open end of the hollow body 412. The pouch 444 can alternatively be removably attached to the wafer 420 by suitable mechanical fasteners 447 such as threading, detents, hook and loop type fasteners, releasable adhesives, and the like.

Referring again to the stomal device 10 of FIGS. 1 and 2, in operation a medical provider (e.g., a surgeon) places the stomal device 10 at a pre-determined stoma site (FIG. 1) for a loop stoma at the time of the initial loop ileostomy/colostomy surgery. In order to implant the stomal device 10, a circular skin incision is made at the pre-determined stoma site. To establish safe entry into the abdomen, the incision is deepened, and the muscles split or separated rather than cut, after which the stomal device is inserted, either intact or in modular fashion, into the incision. In particular, the stomal device is inserted, leading with the first flange, into the incision. As shown in FIG. 1, the hollow body 12 is configured for insertion into a surgical incision provided, e.g., in the abdominal wall. The first flange 14 is configured for releasably retaining the body in the surgical incision when the hollow body is inserted into the surgical incision, and the second flange 16 is configured for resting atop a patient's skin when the hollow body is inserted into the surgical incision. Once the hollow body 12 is implanted, the first flange 14 extends radially from the hollow body about the interior of the abdominal wall and the second flange 16 extends radially from the midportion about the exterior of the abdominal wall, i.e., atop a patient's skin. To insert the stomal device, the user folds or compresses the stomal device so as to allow it to pass through the incision site. Upon passing the lower surface of the abdominal wall, the first flange 14 is released from the confines of the incision and unfolds radially outwardly from the incision. Concurrently, the second flange 16 comes to rest on the patient's skin. Referring to FIG. 1, after gaining access to the abdominal cavity, implantation of the stomal device allows for a loop of a bowel (large or small) to be brought out of the abdomen through the hollow body 12. The pin 18 can then be placed beneath the bowel loop to support the bowel loop exteriorly of the abdomen for easy access by the medical provider.

Referring to FIG. 9 in connection with stomal device 410, following implantation of the hollow body, sutures 500 are used to connect the open edges of the bowel loop 1004 to the second flange 416 to keep the stoma in the bowel loop open. That is, the user sutures with non-absorbable suture the open edges of the bowel loop to the second flange of the stomal device. The user subsequently applies the wafer 420 to the skin around the incision site (FIG. 4). Specifically, the central opening 440 of the wafer 420 is slid over the bowel loop whereupon the wafer is then placed against the patient's skin (and optionally secured thereto by a suitable bio-compatible adhesive). Advantageously, the wafer 420 prevents or inhibits the formation of scar tissue around the stoma as it separates the abdominal wall (and skin) from the bowel. This provides a significant benefit as if scar tissue were permitted to form, surgery may be required to detach the bowel from the abdominal wall (or skin). If the user elects to use the pouch, then the user can removably connect the pouch 444 to the wafer periodically to enable removal and disposal of any fluid and/or waste material from the patient.

When the reversal of the stoma is required, the pin 418 is withdrawn from the through holes in or adjacent to the second flange 416 and the bowel loop retracts into the abdomen of the patient. The wafer 420 is then removed to expose the plurality of sutures 500. The plurality of sutures is then removed and the stomal device 410 is withdrawn from the incision. Thereafter, sutures can be placed to close the bowel loop opening.

Due to the construction and operation of the stomal device, the device ensures ease of use and allows for a rapid surgical procedure to reverse a loop stoma in the operating room, or even in an office or clinic setting. Advantageously, the stomal device can be installed either intact, or alternatively, in a modular fashion to minimize the size of an incision at the stoma site. Such a rapid surgical procedure can eliminate the need for a post-operative hospitalization to recover from said procedure.

Figure 10:
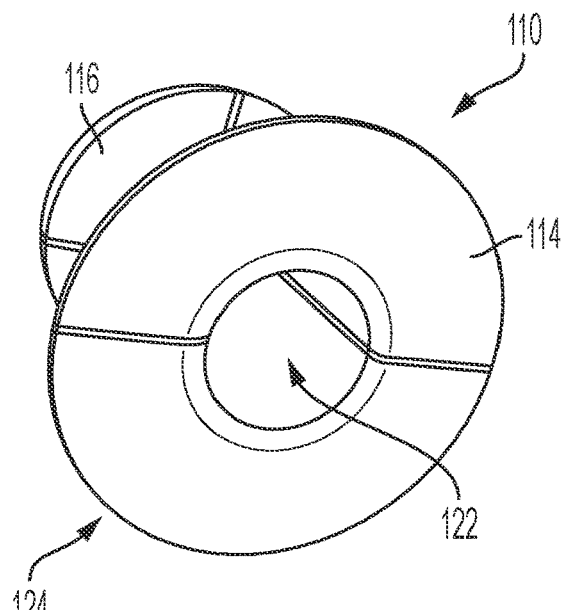
FIG. 10 is a bottom perspective view of another exemplary embodiment of a stomal device in accordance with the subject disclosure.
Figure 11:
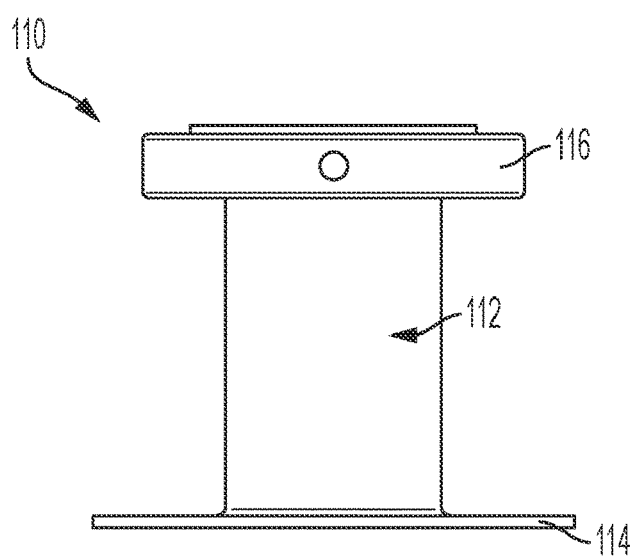
FIG. 11 is an elevational view of the stomal device of FIG. 10.
Figure 12:
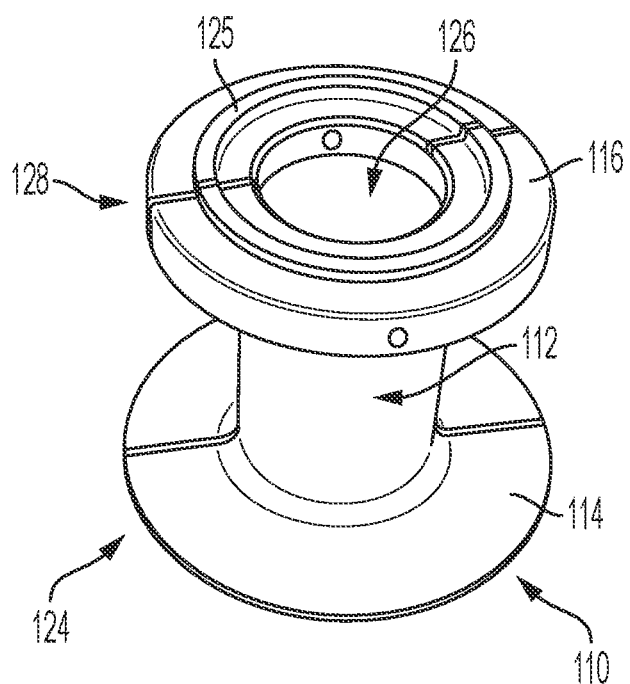
FIG. 12 is a top perspective view of the stomal device of FIG. 10.

FIGS. 10-12 illustrate another exemplary embodiment of a stomal device 110 in accordance with the subject disclosure. This stomal device 110 operates and includes features substantially as disclosed for stomal device 10, except as specifically discussed hereinafter.

The stomal device 110 is generally configured as best shown in FIGS. 10-12 and includes an elongated hollow body 112, a first flange 114 and a second flange 116. The stomal device 110 can be formed of a flexible and/or pliable material such as those discussed for the above embodiments including silicone, or other inert and non-reactive materials. In the present embodiment shown in FIGS. 10-12, the entire stomal device 110 is formed from the same material e.g., silicone, polytetrafluoroethylene (PTFE), perfluoroalkoxy alkanes (PFA), THV (a polymer of tetrafluoroethylene, hexafluoropropylene and vinylidene fluoride), polyamide (PA), ethylene vinyl acetate (EVA), cyclic olefin copolymers (COCS), flexible polyvinyl chloride (PVC), or flexible polyurethane. In other words, the stomal device 110 is formed as a unitary construct. Alternatively, the stomal device 110 can be formed as separate components later secured together e.g., via welding or an adhesive. Having the entire stomal device formed out of e.g., silicone, allows for the stomal device to be easily flexible and foldable to facilitate implantation and removal of the stomal device thereby allowing for a smaller or reduced size incision at the pre-determined stoma site.

The elongated hollow body 112 includes a first open end 122 about its first end 124 and a second open end 126 about its second end 128 opposite the first end. The first and second open ends are in fluid communication. The hollow body 112 is substantially tubular or tubular, and may have constant overall and inner diameter throughout its entire longitudinal length. The hollow body may have a height substantially the same as the height of the hollow body 12 of the stomal device 10 described above. The aperture size opening or inner diameter of the hollow body may range from about 2.5 to 3.0 cm, including 2.4, 2.6, 2.7, 2.8, 2.9, and 3.1 cm, although for an obese patient the inner diameter can be large than 3.1 cm The first flange or inner flap 114 is a radially extending flange that extends from the first end 124 of the hollow body 112. As illustrated, the first flange 114 is configured as a thin annular ring extending radially from the first end of the hollow body. The first flange can have a thickness that ranges from about 1.0 mm to 2.0 mm, including 0.9, 1.1, 1.2, 1.3, 1.4, 1.5, 1.6, 1.7, 1.8, 1.9, and 2.1 mm. The outer diameter of the first flange may range from about 6.5 cm to 7.5 cm, including 6.4, 6.6, 6.7, 6.8, 6.9, 7.0, 7.1, 7.2, 7.3, 7.4, and 7.6 cm.

The second flange or outer flap 116 is a radially extending flange that extends from the second end 128 of the hollow body 112. The second flange 16 can be configured as a substantially planar flange extending radially outwardly. The second flange is configured to be thicker than the first flange so as to accommodate through holes 136 for receiving an unillustrated pin, similar to pin 18 described above, which is used to support a portion of a bowel. Specifically, the thickness of the second flange may range from about 0.8 cm to 1.2 cm, including 0.7, 0.9, 1.0, 1.1, and 1.3 cm. The outer diameter of the second flange may range from about 5.0 to 6.0 cm, including 4.9, 5.1, 5.2, 5.3, 5.4, 5.5, 5.6, 5.7, 5.8, 5.9, and 6.1 cm. The second flange can also include a substantially circular rib 125 (FIG. 12) extending from its outer or upper side for facilitating connection to an unillustrated wafer similar to wafer 20, described above. The circular rib 125 is spaced from an outer circumference of the second flange and/or spaced from an inner surface of the annular second flange. So constructed, the second flange has an overall diameter that is less than an overall diameter of the first flange.

Figure 13A:
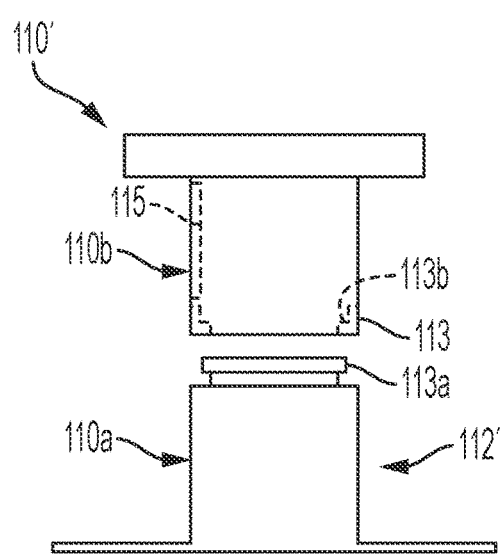
FIG. 13A is an elevational view of a modular stomal device in a disassembled condition in accordance with another exemplary embodiment of the subject disclosure.
Figure 13B:
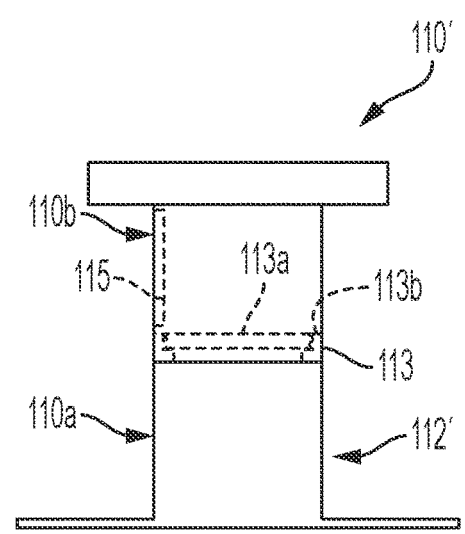
FIG. 13B is an elevational view of the modular stomal device of FIG. 13A in an assembled condition.

As shown in FIGS. 13A and 13B, the stomal device can alternatively be configured as a modular stomal device 110'. That is, the stomal device can be comprised of at least two portions e.g., a first portion 110*a* and a second portion 110*b*. The two body portions 110*a* and 110*b* can have varying tubular body heights to enable a user to select the appropriate overall height of the hollow body portion to closely accommodate a particular patient's abdominal wall thickness. In this configuration, the stomal device also includes fasteners 113 for releasably securing the first and second portions together. For example, the fasteners can include cooperating detents 113*a*, 113*b* or an adhesive, and the like suitable for its intended use. Alternatively, the stomal device 110' can include a plurality of fasteners 115 extending along a longitudinal length of the hollow body portions to allow for variable adjustment of the overall height of the hollow body by a user. All other aspects of the stomal device 110' are similar to that described above for stomal device 110.

In accordance with another aspect of this stomal device 110', when pressure is applied to the body 112' or when the body 112' of the stomal device is squeezed, the two portions of the body 112' are separable due to the detents 113*a*, 113*b* moving apart from each other. When pressure to the body 112' is released, the two portions of the body 112' can be secured together due to the cooperating connection structure, e.g., via the detents 113*a*, 113*b* coming into interlocking engagement as shown in FIG. 13B.

The modular construction of the stomal device 110' advantageously accommodates patients and stoma sites of varying abdominal wall thicknesses and allows for small incision sites. Moreover, the modular nature of the stomal device facilitates easy step-wise removal of the device when a stoma is no longer needed.

FIGS. 14-17 illustrate another exemplary embodiment of a stomal device 210 in accordance with the subject disclosure. The stomal device 210 includes a hollow body 212, a first flange 214, a second flange 216, and a pin 218. This embodiment of the stomal device 210 operates and includes features substantially as disclosed for the above embodiments, except as specifically discussed hereinafter.

The hollow body 212 of the stomal device 210 can be constructed and dimensioned similar to the hollow body 112 of the stomal device 110 described above. Likewise, the second flange 216 of the stomal device 210 can be constructed and dimensioned similar to the second flange 116 of the stomal device 110 (see FIG. 17).

Figure 14:
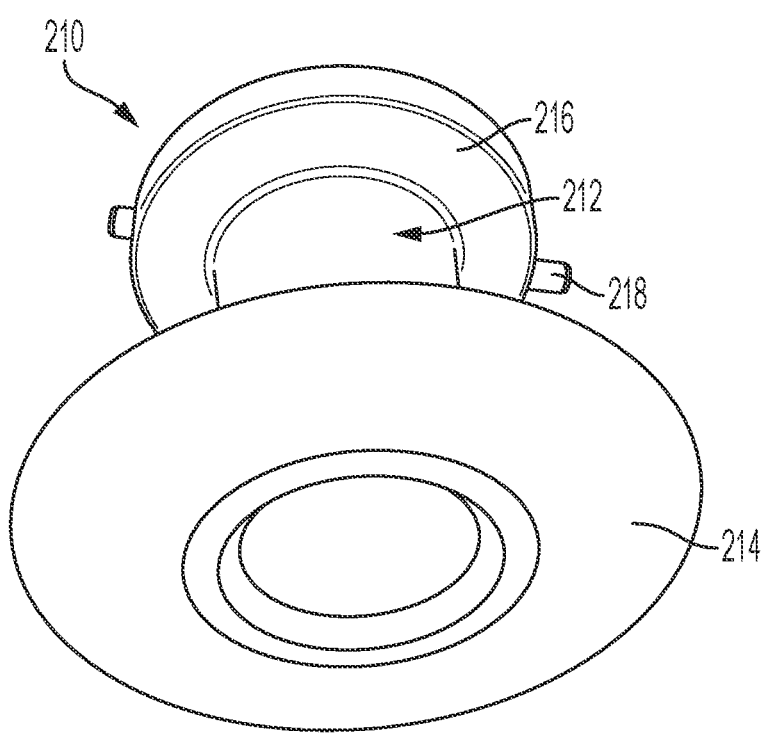
FIG. 14 is a bottom perspective view of another exemplary embodiment of a stomal device in accordance with the subject disclosure.
Figure 15:
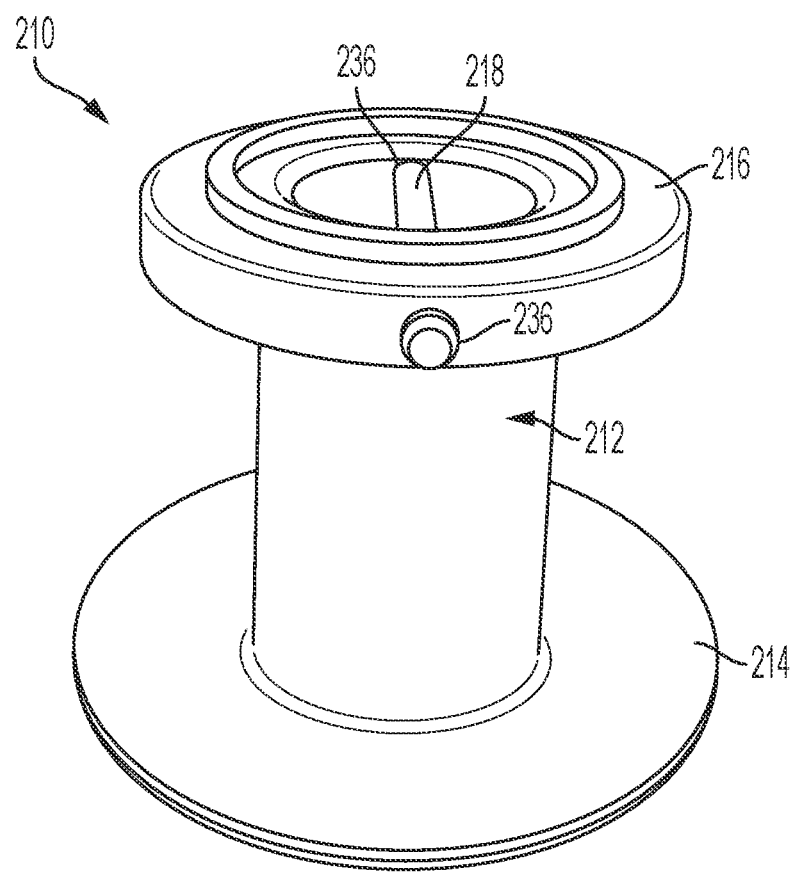
FIG. 15 is a top perspective view of the stomal device of FIG. 14.
Figure 16:
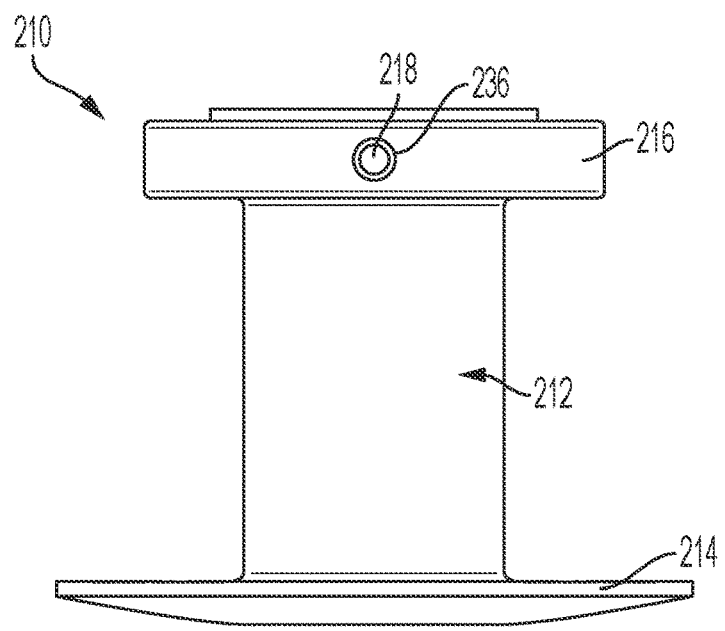
FIG. 16 is an elevational view of the stomal device of FIG. 14.
Figure 17:
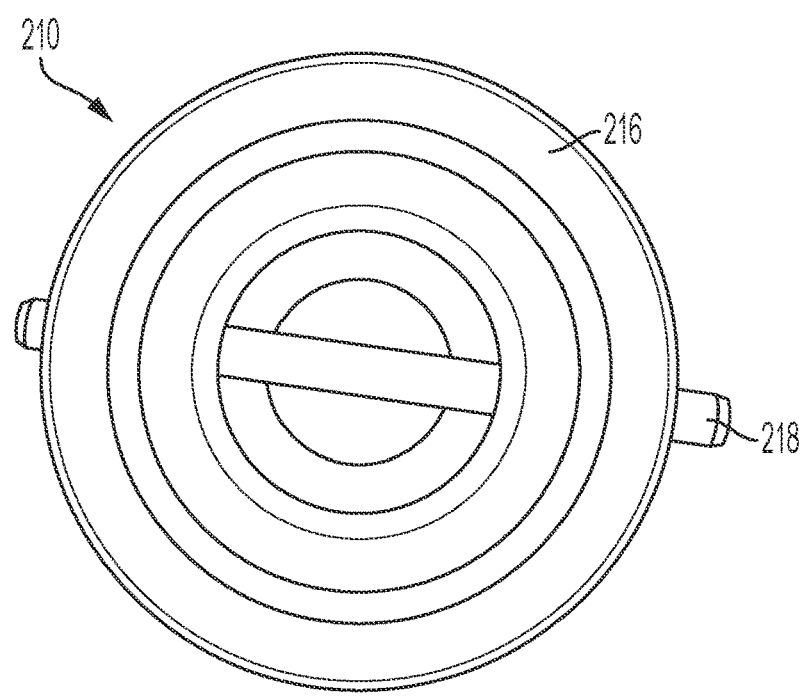
FIG. 17 is a top plan view of the stomal device of FIG. 14.

The first flange 214 of the stomal device 210 is constructed as best shown in FIGS. 14-16. The first flange 214 is structured in a Belleville washer-like manner having a tapered bottom surface. The tapered bottom surface facilitates insertion of the stomal device into the incision. The top surface of the first flange 214 is configured as a planar surface. The first flange can have a maximum thickness that ranges from about 2.0 to 3.0 mm, and a minimum thickness from about 1.0 mm to 2.0 mm about its peripheral end. The outer diameter of the first flange may range from about 6.5 cm to 7.5 cm, including 6.4, 6.6, 6.7, 6.8, 6.9, 7.0, 7.1, 7.2, 7.3, 7.4, and 7.6 cm.

The stomal device 210 can be formed from a flexible, pliable and resilient material including, for example, silicone, polytetrafluoroethylene (PTFE), perfluoroalkoxy alkanes (PFA), THV (a polymer of tetrafluoroethylene, hexafluoropropylene and vinylidene fluoride), polyamide (PA), ethylene vinyl acetate (EVA), cyclic olefin copolymers (COCS), flexible polyvinyl chloride (PVC), flexible polyurethane, or other inert and non-reactive materials. Alternatively, the stomal device 210 can be formed from a suitable rigid material, e.g., a metal, a rigid polymer, or a composite.

In operation, due to the flexible material used to form the stomal device 210 e.g., silicone, the stomal device can be collapsed or folded to facilitate implantation of into the incision in the abdominal cavity. After insertion, pressure to the body 212 is released to allow the stomal device to return to its original uncollapsed shape.

Thereafter the open edges of the stoma are sutured with non-absorbable stitches to the second flange 216 (similar to the suturing of the open edges of the stoma described above in connection with FIG. 9) to secure the stomal device in place. After gaining access to the abdominal cavity, the stomal device 210 allows for a loop of a bowel (large or small) to be brought out of the abdomen through a central cavity or through the hollow body 212.

The pin 218 is constructed as or similar in construction to that of pin 18 and 418 discussed above. Similar to the pins discussed above, the pin 218 allows for the user a means to support a bowel therein during treatment of a patient. When access to the bowel is no longer needed, the pin 218 can be withdrawn through the through holes 236 of the second flange 216 to remove the pin and allow the bowel to retract back into the abdomen.

FIGS. 18, 19A, 19B, 20A and 20B illustrate another exemplary embodiment of a stomal device 310 in accordance with the subject disclosure. The stomal device 310 includes a hollow body 312 having a first flange 314, a second flange 316, and a balloon 370. This embodiment of the stomal device 310 operates and includes features substantially as disclosed for the above embodiments, except as specifically discussed hereinafter. The stomal device 310 advantageously allows for the closure of an end stoma while also being operable to provide transient/intermittent continence during a temporary end colostomy or end ileostomy surgical procedure.

The hollow body 312, including the first flange and the second flange, can be of a unitary construction formed from a flexible material, such as but not limited to silicone, polytetrafluoroethylene (PTFE), perfluoroalkoxy alkanes (PFA), THV (a polymer of tetrafluoroethylene, hexafluoropropylene and vinylidene fluoride), polyamide (PA), ethylene vinyl acetate (EVA), cyclic olefin copolymers (COCS), flexible polyvinyl chloride (PVC), flexible polyurethane, or other inert and non-reactive materials. Alternatively, the hollow body can be formed from a suitable rigid material, e.g., a metal, a rigid polymer, or a composite. The hollow body 312 allows the user to draw out an end portion of a bowel (e.g., colon or small intestine) from the abdomen that will form an opening or stoma (FIG. 18).

The elongated hollow body 312 is generally configured as best shown in FIG. 19. The hollow body includes a first open end 322 about its first end 324 and a second open end 326 about its second end 328 opposite the first end. The first and second open ends are in fluid communication. The hollow body 312 is substantially tubular. As shown in FIG. 18, the hollow body can also be configured to have a curved cone shape including substantially curved cone shaped ends or portions 330, 332. The hollow body is structured to have an overall height of about 5.0 to 6.0 cm, including 4.9, 5.1, 5.2, 5.3, 5.4, 5.5, 5.6, 5.7, 5.8, 5.9, and 6.1 cm, although in a thin patient the height of the hollow body can be smaller and for an obese patient the height of the hollow body can be larger. The hollow body is also structured to have an overall outer diameter from about 2.9 to 3.3 cm, including 2.7, 2.8, 3.0, 3.1, 3.2 and 3.4 cm. Further, about its mid-section, the hollow body is structured to have an inner diameter or aperture opening size from about 2.5 to 3.0 cm, including 2.6, 2.7, 2.8 and 2.9 cm, although for an obese patient the inner diameter can be larger. The mid-section is smaller than the overall diameter of the hollow body about its respective ends.

The first flange or inner flap 314 is a radially extending flange that extends from the first end 324 of the hollow body 312. The first flange 314 can be a tapered flange having a tapered outer side such that it gradually extends outwardly from the first end forming a substantially curved cone shaped end, or it can alternatively be configured as a substantially planar flange extending radially outwardly.

The second flange or outer flap 316 is a radially extending flange that extends from the second end 328 of the hollow body 312. The second flange 316 can be a tapered flange such that it gradually extends outwardly from the second end forming a substantially curved cone shaped end, or it can alternatively be configured as a substantially planar flange extending radially outwardly. According to an aspect, the first flange 314 of the hollow body 312 has an overall diameter greater than the second flange 316. Again, the relatively larger diameter of the first flange serves to resist dislodgement of the hollow body from an incision.

The balloon 370 is preferably secured to and extends from the first flange 314 of the stomal device. More particularly, the balloon extends from an inner surface of the hollow body adjacent the first flange. The balloon 370 can be an annular-shaped balloon having an inner through hole configured to move between a first overall diameter and a second overall diameter smaller than the first overall diameter. The balloon 370 is also formed from an elastic material that allows the balloon to increase its volume when inflated from an initial volume of 1× (FIG. 20A) to an expanded volume (FIG. 20B) of 2X, 3X, 4X, 5X or more of the initial volume. In doing so, the overall diameter of the through hole decreases when going from the initial volume to the expanded volume. The balloon when inflated can change its inner through hole diameter from e.g., about 2.5 cm to about 5 mm.

Referring to FIGS. 19A and 19B, the balloon also includes an elongated nozzle 372 extending therefrom for use in inflating and deflating the balloon. The nozzle 372 includes an inlet 374 that is position adjacent a top end of the second flange. The nozzle also includes a valve 375 for inflating or deflating the balloon. For example, the valve may be adapted to accept a syringe (not shown) for injecting or withdrawing air or another gas into the balloon. The hollow body 312 includes a channel 376 within which the nozzle extends through and the valve resides. The channel has a length sized sufficiently to extend from about the first flange to the second flange as shown in FIG. 19A. That is, channel extends along a longitudinal extent of the hollow body 312.

As described above in relation to the stomal device 410, the stomal device 310 can also include a wafer similar to wafer 420 discussed above for use in preventing or retarding formation of scar tissue around the end stoma.

Figure 20A:
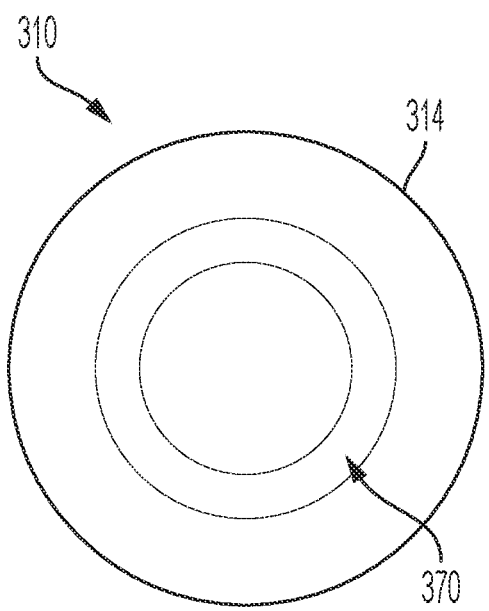
FIG. 20A is a bottom view of the stomal device of FIG. 18 in a first operative condition.
Figure 20B:
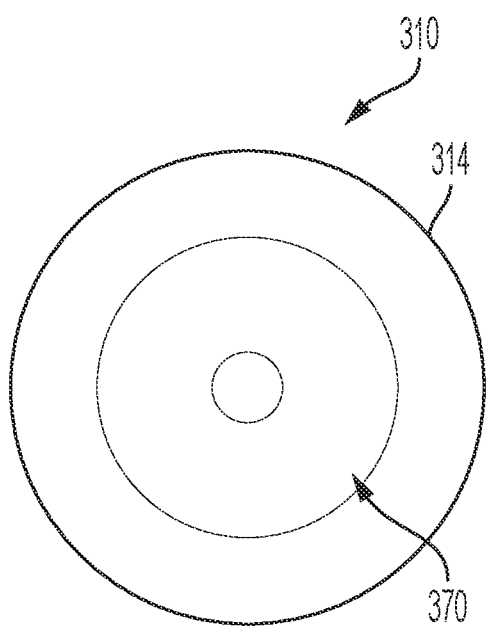
FIG. 20B is a bottom view of the stomal device of FIG. 18 in a second operative condition.

In operation, the stomal device 310 may be implanted at a pre-determined stoma site in a similar fashion as described above for the stomal device 10. The user draws an identified end portion of a bowel from the abdomen through the hollow body of the stomal device. The user then inserts a syringe into the nozzle 372 of the second flange and injects air or another appropriate gas so as to inflate the balloon 370 adjacent the first flange. When inflated (FIG. 20B), the balloon 370 compresses an end portion of the bowel passing through the hollow body to provide temporary continence to the end stoma. Advantageously, the stomal device 310 is operable to provide temporary continence while allowing the patient avoid wearing a stoma pouch bag while the balloon is inflated, as may otherwise be required in traditional temporary end colostomy or end ileostomy surgical procedures. If the user desires to allow the end stoma to evacuate fluid and/or waste material, the user may withdraw air through the nozzle 372 via e.g., a syringe, so as to deflate the balloon (FIG. 20A).

Figure 21:
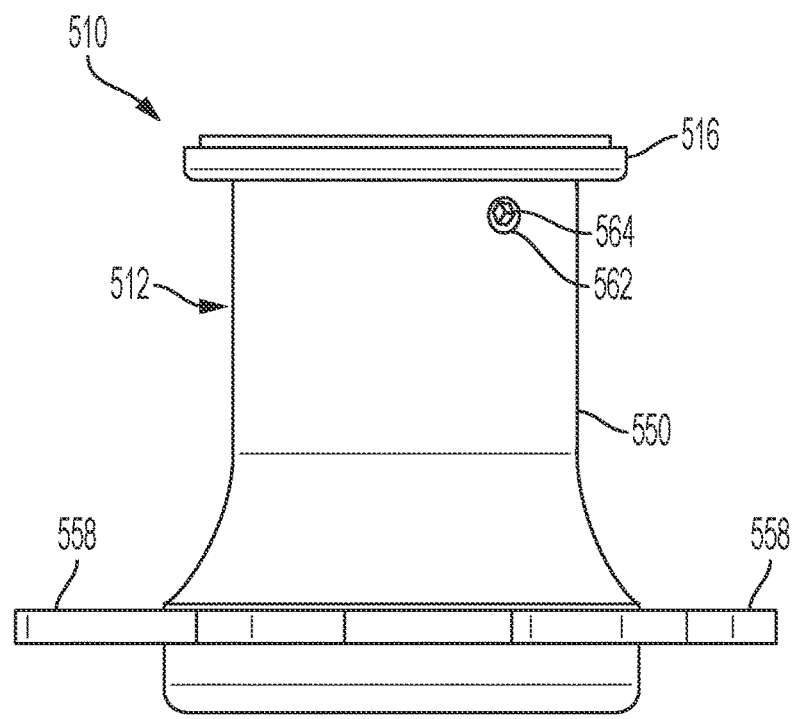
FIG. 21 is an elevational view of another exemplary embodiment of a stomal device in accordance with the subject disclosure.
Figure 22:
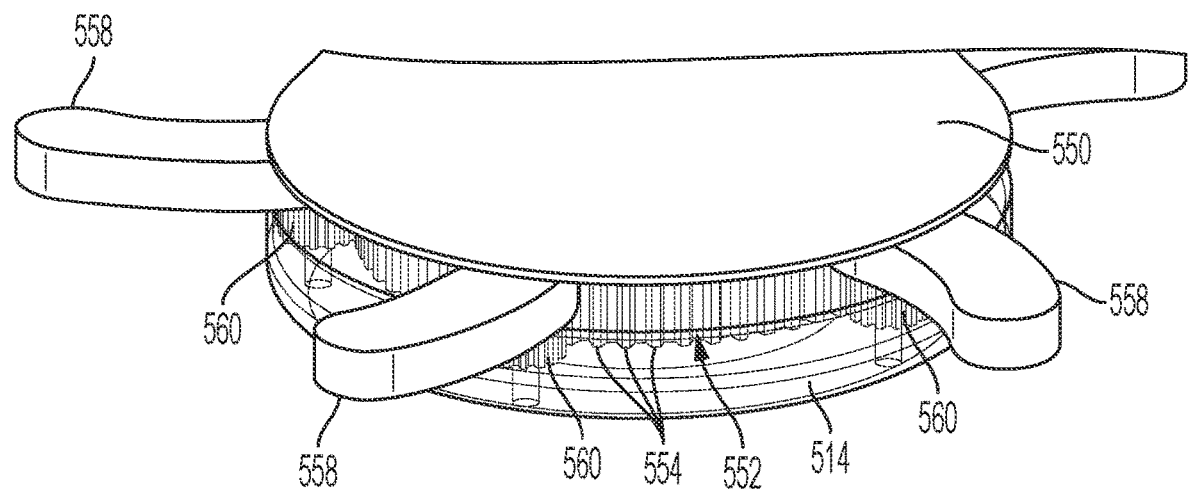
FIG. 22 is an enlarged view of a lower portion of the stomal device of FIG. 21.
Figure 23:
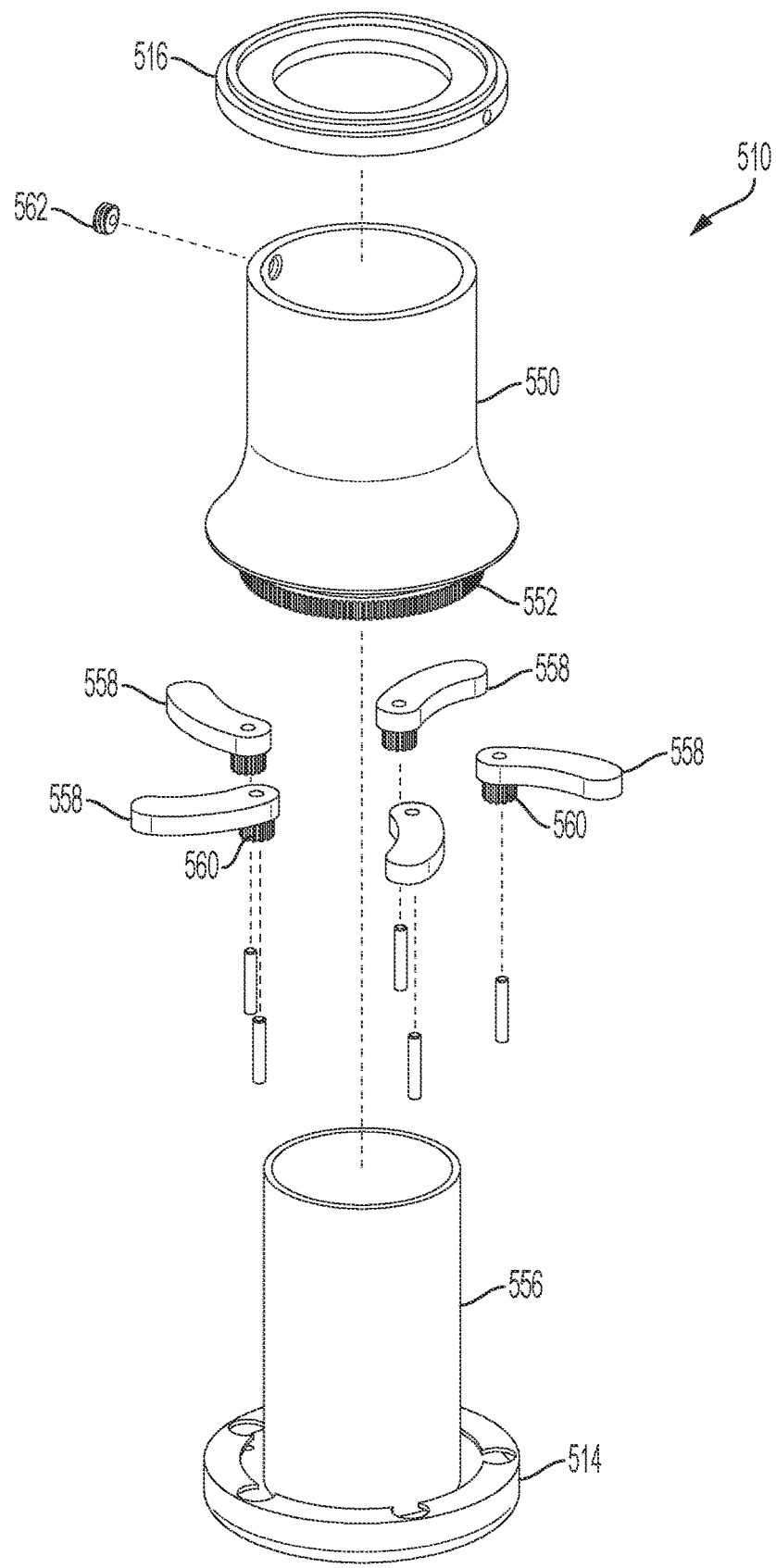
FIG. 23 is an exploded view of the stomal device of FIG. 21.

Referring to FIGS. 21, 22 and 23, there is illustrated a stomal device 510 in accordance with another exemplary embodiment of the subject disclosure. The stomal device 510 includes a hollow body 512, a first flange 514 and a second flange 516. The hollow body has a two-part construction. The first part includes a substantially cylindrical outer body member 550 having an upper end terminating beneath the second flange and an annular gear 552 at its lower end. The annular gear 554 includes gear teeth circumscribing its circumference and is sized to have an overall diameter less than an overall diameter of the outer body member distal end or lower most end. That is, the annular gear 554 has its outer circumference spaced from the outer circumference of the lower most end of the outer body. The second part includes a substantially cylindrical inner body member 556 having an upper end connected to and extending downwardly from the second flange 516 and a lower end connected to the first flange 514. The first flange 514 is a substantially annular flange having a plurality of receptacles for receiving respective arms, as further discussed below. According to an aspect, one of the inner body member and the outer body member is movable relative to the other. For example, the inner body member may rotate relative to the outer body member. The upper portion of the inner and outer body is substantially tubular and the second flange is a substantially planar flange extending from the inner body member. The lower portion of the inner and outer body is substantially curved coned shaped, having an overall diameter larger at its most distal end than the overall diameter of the upper portion of the inner and outer body.

The hollow body, including the first and second flange, can be formed from a suitable rigid material, e.g., a metal, a rigid polymer, or a composite. The overall height and width dimensions of the stomal device 510 are the same or substantially the same as the dimensions of the stomal devices discussed above.

The stomal device 510 further comprises a plurality of radially extendable and retractable arms 558 (which are shown in their extended position in FIGS. 21 and 22). In the present embodiment, the stomal device includes six extendable arms, but can include more or less e.g., 2, 3, 4, 5, 7, and 8. Each arm 558 is connected to a spur gear 560 that is rotatably supported in the first flange 514. The gears 560 meshingly engage with the annular gear 552 of the outer body member to pivot each arm respectively between a retracted position and an extended position. In other words, each arm pivots such that its distal end travels an arc length of about 80-100 degrees including 75, 85, 90, 95 and 105 degrees between the extended and retracted positions.

Figure 24:
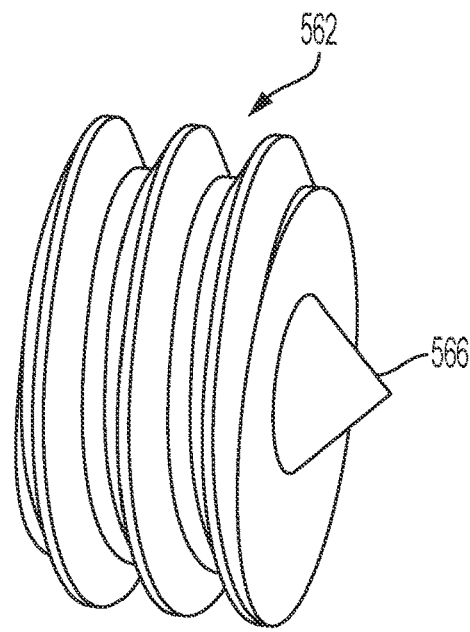
FIG. 24 is an enlarged perspective view of a set screw of the stomal device of FIG. 21.

Additionally, the stomal device comprises a fastener or locking mechanism to secure the outer body member in a fixed position relative to the inner body member. The locking mechanism can be a set screw 562 (FIGS. 21, 23 and 24) that is threadedly engaged with outer body member 550. The outer end of the set screw includes a socket 564 for receiving an unillustrated tool for turning the set screw, and the inner end of the set screw includes a tapered tip 566 for contacting the inner body member 556. Alternatively to the set screw, the locking mechanism can a detent between the inner and outer body members or a threaded engagement between the inner and outer body members.

Prior to implantation of the stomal device 510, if the arms 558 are not already retracted, the second flange 516 is grasped by one of the user's hands and the outer body member 550 is grasped by the other of the user's hands. The user then rotates the outer body member in a first direction relative to the second flange to retract the arms 558 into the first flange 514 or into the retracted position. With the arms 558 retracted, the stomal device is configured for implantation into an incision. The stomal device 510 is implanted similar to stomal devices 10 and 410 described above. That is, the first flange 514 is inserted into the incision until it passes beneath the inner surface of the abdominal wall and the second flange 516 comes to rest on the patient's skin. Once the stomal device is implanted, the user rotates the outer body member in a second direction relative to the second flange to extend the arms 558 radially outwardly of the first flange 514 whereby they assume the position shown in FIGS. 21 and 22. The user then tightens the set screw 562 until it comes into firm engagement with the inner body member 556, thereby locking the arms into a radially extended position. The radially extended arms 558 operate to resist inadvertent dislodgement of the stomal device 510 from the incision.

Once implanted, the hollow body 512 allows the user to draw out a loop of a bowel from the abdomen that will form an opening or stoma. An unillustrated pin, similar to pin 18 or 418 described above is inserted through unillustrated opposed through holes provided in the second flange 516 and beneath the bowel loop to support the bowel loop exteriorly of the patient's body. A wafer similar to wafer 420 described above is then placed around the stoma and atop the second flange and a pouch similar to pouch 444 may be connected to the wafer in the manner described above.

When it is desired to reverse the stoma, the pouch and wafer are removed and the stoma is sutured shut. The pin is then withdrawn whereupon the bowel loop retracts into the abdomen. The set screw 562 is then loosened and the outer body member is turned in a direction to retract the arms 558 into the first flange 514. The stomal device is then withdrawn from the incision and the incision is sutured shut.

Figure 25:
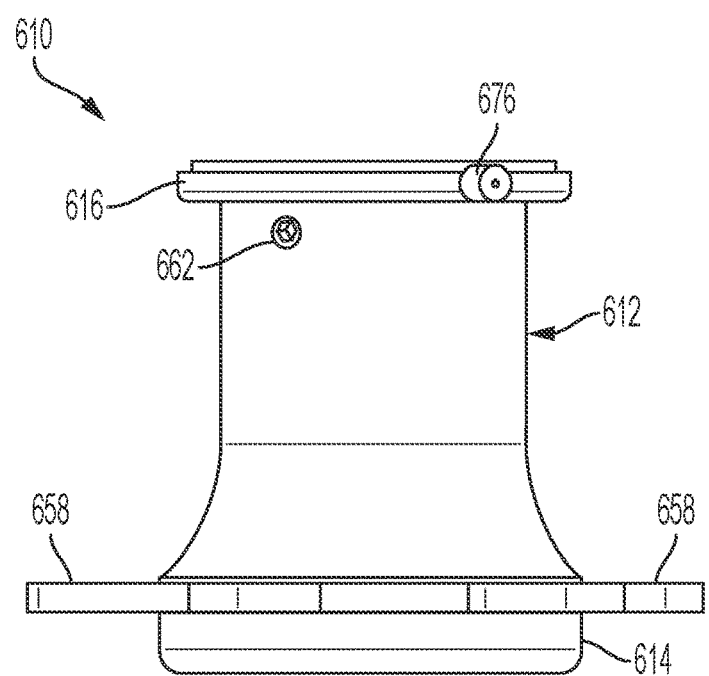
FIG. 25 is an elevational view of another exemplary embodiment of a stomal device in accordance with the subject disclosure.
Figure 26:
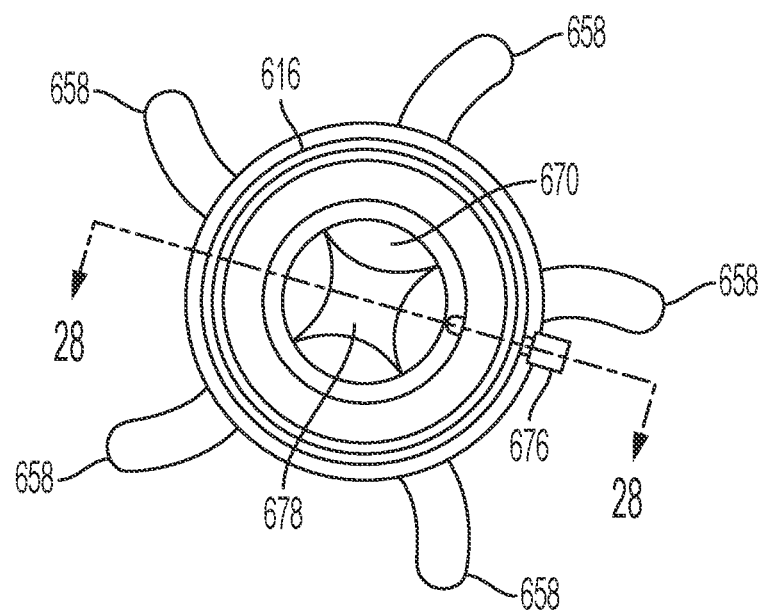
FIG. 26 is a top view of the stomal device of FIG. 25.
Figure 28:
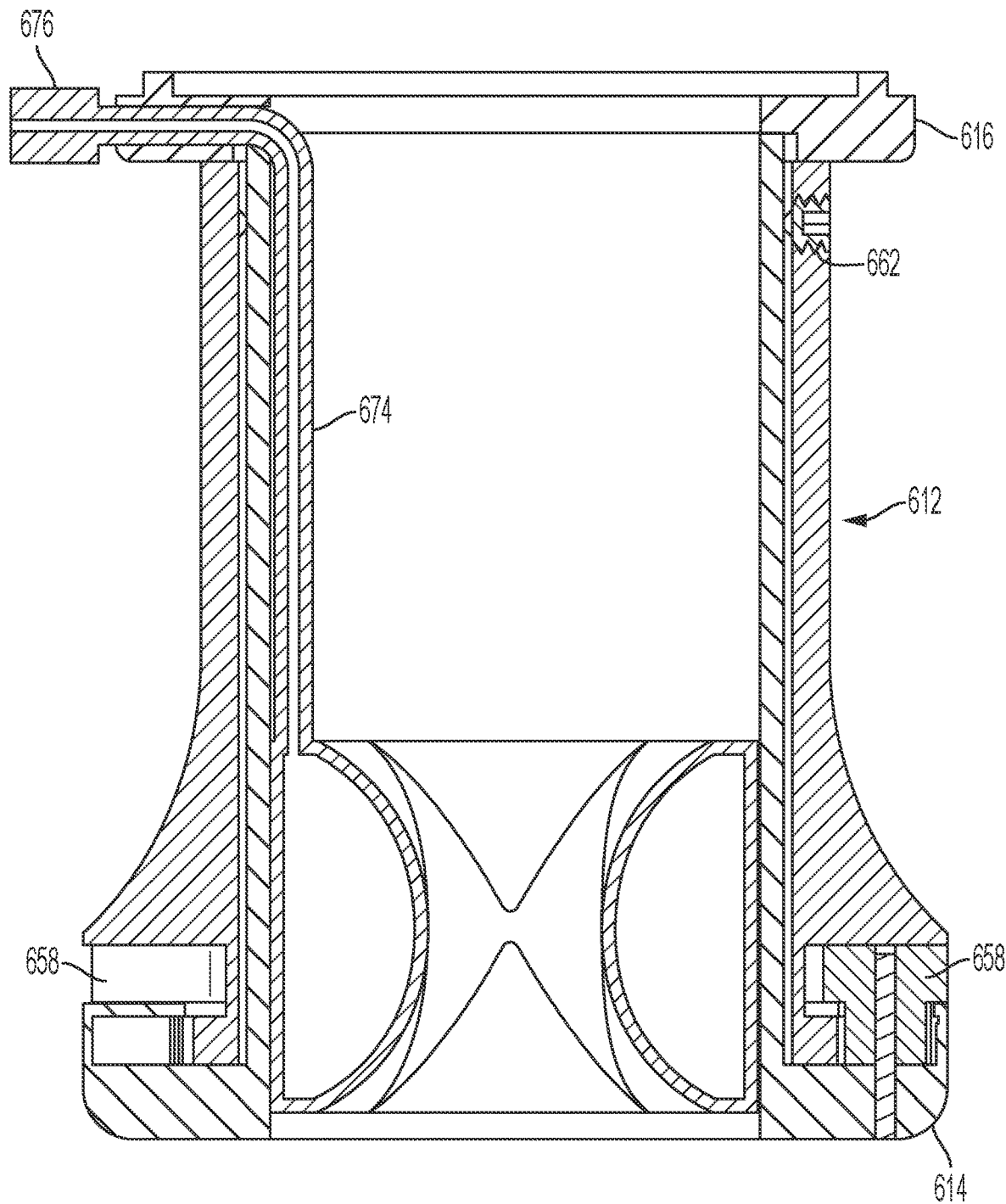
FIG. 28 is an elevational cross-sectional view of the stomal device of FIG. 25 taken along line 28-28 of FIG. 26.

FIGS. 25, 26 and 28 illustrate another exemplary embodiment of a stomal device 610 in accordance with the subject disclosure. The stomal device 610 includes a hollow body 612 having a first flange 614, a second flange 616, and a balloon 670. This embodiment of the stomal device 610 operates and includes features substantially as disclosed for the embodiment of the stomal device 510 described above in connection with FIGS. 21-23, except as specifically discussed hereinafter. The stomal device 610 advantageously allows for the closure of an end stoma while also being operable to provide transient/intermittent continence during a temporary end colostomy or end ileostomy surgical procedure.

About its mid-section, the hollow body 612 is structured to have an inner diameter or aperture opening size from about 2.5 to 3.0 cm, including 2.4, 2.6, 2.7, 2.8, 2.9, and 3.1 cm (although for an obese patient the inner diameter can be larger) which is smaller than the overall diameter of the hollow body about its respective ends. Like stomal device 510, stomal device 610 includes a locking mechanism e.g., a set screw 662 which releasably locks inner and outer body members of the hollow body 612 in a fixed position relative to each other e.g., between first and second positions where arms 658 are either in their radially extended position, as shown in FIG. 25, or in an retracted position (FIG. 28) where the arms are positioned within a circumference defined by the outer edges of the first flange.

Figure 27:
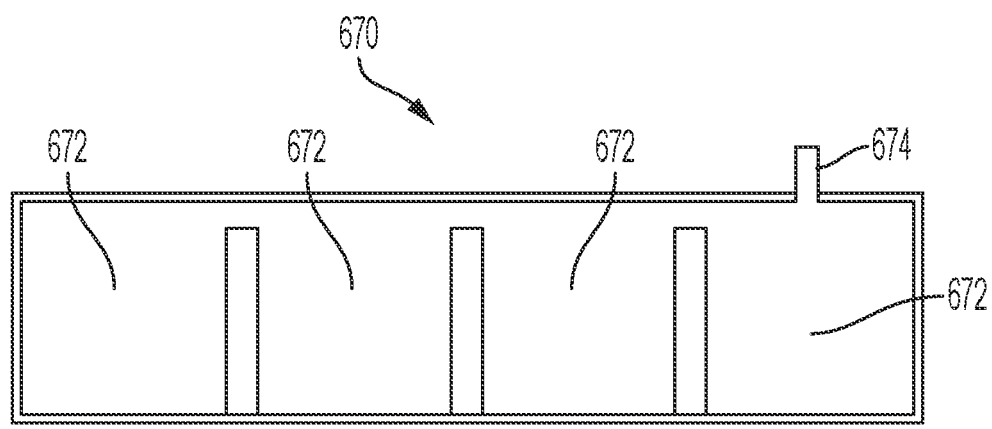
FIG. 27 is an elevational view of a balloon of the stomal device of FIG. 25.

The balloon 670 is carried on an interior wall of the inner body member of the hollow body (FIGS. 26 and 28). As shown in FIG. 27, the balloon includes a plurality of inflatable pockets 672 in fluid communication with one another and a gas, e.g., air fill tube 674, which is in fluid communication with an inflation/deflation valve 676 (FIGS. 25, 26 and 28) positioned within or about the second flange 616. The valve 676 can be constructed similar to an athletic ball inflation/deflation valve. That is, the valve may be formed of flexible material, e.g., silicone, and have a self-sealing orifice that can be penetrated by a syringe tip which enables the balloon to be easily inflated and deflated. The balloon 670 is also formed from an elastic material that allows the balloon to increase its volume when inflated from an initial volume of 1× to an expanded volume (FIGS. 26 and 28) of 2X, 3X, 4X, 5X or more of the initial volume. In doing so, the overall diameter of a bowel-receiving through hole 678 defined by the balloon decreases when going from the initial volume to the expanded volume. The balloon when inflated can change its inner through hole diameter from e.g., about 2.5 cm to about 5 mm.

As described above in relation to the stomal device 410, the stomal device 610 can also include a wafer similar to wafer 420 discussed above for use in preventing or retarding formation of scar tissue around the end stoma.

In operation, the stomal device 610 may be implanted at a pre-determined stoma site and arms 658 are brought into their radially extended positions in a similar fashion as described above for the stomal device 510. The user draws an identified end portion of a bowel from the abdomen through the hollow body of the stomal device. The user then inserts a syringe into the valve 676 and injects air or another appropriate gas so as to inflate the balloon 670. When inflated (FIGS. 26 and 28), the balloon 670 compresses an end portion of the bowel passing through the hollow body to provide temporary continence to the end stoma. Advantageously, the stomal device 610 is operable to provide temporary continence while allowing the patient to avoid wearing a stoma pouch bag while the balloon is inflated, as may otherwise be required in traditional temporary end colostomy or end ileostomy surgical procedures. If the user desires to allow the end stoma to evacuate fluid and/or waste material, the user may withdraw air through the valve 676 via e.g., a syringe, so as to deflate the balloon.

The subject disclosure describes stomal devices for facilitating a stoma or reversal of a stoma. The stomal device can include a unitary or a modularly constructed stomal device. Advantageously, the stomal device can be installed either as a single construct, or alternatively, in a modular fashion to minimize the size of an incision at the stoma site.

If modular in nature, the multi-segmented (i.e., modular) construction of the stomal devices advantageously accommodates patients and stoma sites of varying abdominal wall thicknesses. Moreover, the modular nature of the stomal devices facilitates step-wise removal of the device when a stoma is no longer needed. Accordingly, the stomal devices of the subject disclosure reduces the need for an invasive surgical procedure, for example, in an operating room or similar setting, to reverse or close the stoma. Instead, the user may perform closure of the stoma in an office or clinic setting, thereby reducing recovery time such as hospitalization for several days. It is contemplated that fascial stitches and bowel purse string sutures may be utilized for closure after removal of the stomal device.

The subject disclosure also describes a method for implanting a stomal device and for facilitating reversal of a stoma. The implantation method includes, forming an incision site to receive a stomal device, inserting the stomal device of the subject disclosure through the incision site, withdrawing a portion of a bowel through the stomal device, inserting a pin below a loop of a bowel and through the stomal device to prevent the bowel loop from retracting back into the abdomen of a patient. Additionally, the method can include the steps of withdrawing the pin from the flange or hollow body of the stomal device, retracting the bowel loop back into the abdomen of the patient, and withdrawing the stomal device from the patient.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

I claim:

1. A stomal device comprising:
   an elongated hollow body having a first open end about its first end and a second open end in fluid communication with the first open end about its second end opposite the first end;
   a first flange extending from the first end of the hollow body;
   a second flange extending from the second end of the hollow body; and
   a pin for extending through the second flange transverse to a longitudinal direction of the hollow body.

2. The stomal device of claim 1, wherein the hollow body is substantially tubular.

3. The stomal device of claim 1, wherein the hollow body is curved cone shaped.

4. The stomal device of claim 1, wherein the hollow body includes a pair of curved cone shaped portions.

5. The stomal device of claim 1, wherein the hollow body is modular.

6. The stomal device of claim 5, wherein the hollow body comprises a first body portion connectable to a second body portion.

7. The stomal device of claim 1, wherein the first flange is a tapered flange.

8. The stomal device of claim 7, wherein the tapered flange includes a tubular inner side and tapered outer side.

9. The stomal device of claim 1, wherein the second flange includes a substantially circular rib extending from its outer side.

10. The stomal device of claim 1, further comprising a wafer adjacent the second flange.

11. The stomal device of claim 10, wherein the wafer includes a central opening in fluid communication with the second open end.

12. The stomal device of claim 1, further comprising a pouch that includes an opening attachable to the first flange such that the opening is in fluid communication with the first open end.

13. The stomal device of claim 1, wherein the hollow body is flexible.

14. The stomal device of claim 1, wherein the hollow body is formed from silicone, polytetrafluoroethylene (PTFE), perfluoroalkoxy alkanes (PFA), THV (a polymer of tetrafluoroethylene, hexafluoropropylene and vinylidene fluoride), polyamide (PA), ethylene vinyl acetate (EVA), cyclic olefin copolymers (COCS), flexible polyvinyl chloride (PVC), or flexible polyurethane.

15. The stomal device of claim 1, wherein the first flange has an overall diameter greater than the second flange.

16. The stomal device of claim 1, wherein the second flange includes opposed through holes for receiving the pin therein.

17. The stomal device of claim 1, wherein the pin has a length greater than an overall diameter of the second flange.

18. The stomal device of claim 1, further comprising a balloon extending from the first flange.

19. The stomal device of claim 18, further comprising a nozzle operatively connected to the balloon having an inlet adjacent the second flange.

20. The stomal device of claim 1, further comprising a balloon carried by an interior of the hollow body.

21. The stomal device of claim 1, further comprising a plurality of radially extendable arms adjacent the first flange.

22. The stomal device of claim 1, wherein the hollow body comprises an inner body member and an outer body member, and wherein one of the inner body member and the outer body member is movable relative to the other.

23. The stomal device of claim 22, wherein the outer body member includes a lower end having an annular gear.

24. The stomal device of claim 23, further comprising a plurality of extendable arms each having a spur gear engaged with the annular gear.

25. The stomal device of claim 22, further comprising a locking mechanism for securing the outer body member in a fixed position relative to the inner body member.

* * * * *